(12) United States Patent
Litman

(10) Patent No.: US 7,244,453 B1
(45) Date of Patent: Jul. 17, 2007

(54) ANTI-CHLORINE SHAMPOO COMPOSITION

(76) Inventor: Lucia Mihalchick Litman, 7227 Lewis Ridge Pkwy., Edina, MN (US) 55439

(*) Notice: Subject to any disclaimer, the term of this patent is extended or adjusted under 35 U.S.C. 154(b) by 0 days.

(21) Appl. No.: 11/338,188

(22) Filed: Jan. 24, 2006

(51) Int. Cl.
*A61K 36/81* (2006.01)

(52) U.S. Cl. .................... 424/773; 424/725; 424/74

(58) Field of Classification Search .................... None
See application file for complete search history.

(56) References Cited

U.S. PATENT DOCUMENTS

| | | | |
|---|---|---|---|
| 3,730,912 A | 5/1973 | Inamorato | |
| 4,132,680 A | 1/1979 | Nicol | |
| 4,247,538 A | 1/1981 | Barker | |
| 4,264,457 A | 4/1981 | Beeks et al. | |
| 4,273,760 A | 6/1981 | Koehler et al. | |
| 4,295,985 A | 10/1981 | Petrow et al. | |
| 4,298,480 A | 11/1981 | Wixon | |
| 4,333,862 A | 6/1982 | Smith et al. | |
| 4,338,204 A | 7/1982 | Spadini et al. | |
| 4,436,653 A | 3/1984 | Jacobsen et al. | |
| 4,659,802 A | 4/1987 | Rubingh et al. | |
| 4,744,977 A | 5/1988 | Hensen et al. | |
| 4,790,856 A | 12/1988 | Wixon | |
| 4,913,828 A | 4/1990 | Caswell et al. | |
| 4,931,216 A | 6/1990 | Igarashi et al. | |
| 5,145,607 A | 9/1992 | Rich | |
| 5,204,010 A | 4/1993 | Klewsaat | |
| 5,324,862 A | 6/1994 | Yokota et al. | |
| 5,332,854 A | 7/1994 | Yokota et al. | |
| 5,344,949 A | 9/1994 | Koerner et al. | |
| 5,441,541 A | 8/1995 | Mehreteab et al. | |
| 5,472,455 A | 12/1995 | Mehreteab et al. | |
| 5,565,145 A | 10/1996 | Watson et al. | |
| 5,607,980 A | 3/1997 | McAtee et al. | |
| 5,610,187 A | 3/1997 | Manning et al. | |
| 5,622,925 A | 4/1997 | De Buzzaccarini et al. | |
| 5,661,189 A | 8/1997 | Grieveson et al. | |
| 5,747,436 A | 5/1998 | Patel et al. | |
| 5,939,059 A | 8/1999 | Franklin et al. | |
| 5,997,854 A | 12/1999 | Von Mallek | |
| 6,007,802 A | 12/1999 | Coffindaffer et al. | |
| 6,555,139 B2 | 4/2003 | Sharma | |
| 6,861,077 B1 * | 3/2005 | Cannell et al. | ............. 424/725 |
| 2005/0053570 A1 | 3/2005 | Hirai et al. | |

FOREIGN PATENT DOCUMENTS

| | | |
|---|---|---|
| WO | WO 96/37591 | 5/1996 |
| WO | WO 97/12022 | 9/1996 |
| WO | WO 97/15647 | 9/1996 |
| WO | WO 97/28238 | 12/1996 |

* cited by examiner

*Primary Examiner*—Susan Hoffman
(74) *Attorney, Agent, or Firm*—Mark A. Litman & Associates, P.A.

(57) ABSTRACT

Retention of chlorine and hypochlorite in hair is reduced by treating the hair with a defined composition, allowing the composition to remain on the hair for at least 10 seconds, and then rinsing off the composition with water. The composition comprises at least 1% by total weight of the composition of potato particles having an average diameter of less than 10 microns when dried; at least 1% by total weight of the composition of clathrate; at least 1% by weight of surfactant; and water.

4 Claims, No Drawings

ANTI-CHLORINE SHAMPOO COMPOSITION

BACKGROUND OF THE ART

1. Field of the Invention

The present invention relates to the field of hair protection from chlorine after swimming in chlorinated swimming pools.

2. Background of the Art

Published US Patent Application 20050053570 teaches clathrates as a general ingredient in shampoo, but for an undefined purpose along with many other generic classes of ingredients.

U.S. Pat. No. 4,295,985 (Petrow) discloses a method for removing rapidly chlorine retained by the skin and hair of, for example, swimmers, after exposure to chlorinated water by means of a stoichiometric excess of a suitable reducing agent, such as an alkali thiosulfate and the like in aqueous solution, and with toilet soaps and shampoos comprising said agent adapted to effect said removal. Clathrates were tried in an examples for leaching chlorine from the skin, but were found to be too slow, taking 20 times longer than the proposed ingredients.

General detergent anionic-cationic surfactant mixtures are well known to the art. See generally, U.S. Pat. Nos. 5,441,541, 5,472,455, 5,204,010, 4,790,856, 4,298,480, 3,730,912 (all to The Colgate-Palmolive Company), 5,622,925, 5,607,980, 5,565,145, 4,913,828, 4,659,802, 4,436,653, 4,338,204, 4,333,862, 4,132,680 (all to The Procter & Gamble Co.); also see WO 97/03164, WO 97/12022 and WO 96/37591 (all to The Procter & Gamble Co.), and WO 97/28238 and WO 97/15647 (both to Reckitt & Colman, Inc.). See also, U.S. Pat. Nos. 5,610,187 and 4,247,538 (both to Witco Corp.), 5,344,949 (to Th. Goldschmidt AG), 5,332,854 and 5,324,862 (both to Dai-Ichi Kogoyo Seiyaku Co., Ltd.), 4,273,760 (to National Starch and Chemical), and 4,264,457 (to DeSoto, Inc.).

Compositions comprising anionic-cationic surfactant mixtures are also relatively well known. U.S. Pat. No. 6,007,802 (to Procter & Gamble) discloses a conditioning shampoo composition with excellent cleaning performance and improved levels of conditioning while minimizing any adverse effect associated with build-up; the disclosed compositions general comprise an ethoxylated alkyl sulfate, amphoteric surfactant, insoluble, dispersed conditioning agent (nonionic, cationic silicone), synthetic esters, and cellulosic cationic polymers. U.S. Pat. No. 5,939,059 (to Akzo Nobel) discloses a 2-in-1 conditioning shampoo comprising an anionic surfactant (alkyl sulfate or ether sulfate) and ester quats, with optional amide. U.S. Pat. No. 5,747,436 (to Colgate Palmolive) discloses a low static conditioning shampoo comprising an anionic and an amphoteric surfactant, complex acid:amine (1:1 mole ratio) and polyquaternary compound. U.S. Pat. No. 5,607,980 (to Procter & Gamble) discloses topical compositions having improved skin feel comprising an anionic surfactant (alkyl sulfate, ether sulfate, isethionate), a cationic surfactant and an amphoteric surfactant. U.S. Pat. No. 5,997,854 (to Henkel) discloses a conditioning shampoo formulation comprising a quaternary ammonium component, an emulsifier, an amphoteric, an alkyl polyglycoside surfactant. U.S. Pat. No. 5,145,607 (to Takasago International Corporation) discloses an optically clear conditioning shampoo comprising anionic (alkyl sulfate or alkyl ether sulfate) and cationic surfactants. U.S. Pat. No. 4,931,216 (to Kao Corporation) discloses detergent compositions comprising an anionic or amphoteric surface active agents and a branched quaternary ammonium salt. U.S. Pat. No. 4,744,977 (to Henkel) discloses quaternary ammonium compound hair conditioners in combination with an anionic surfactant. U.S. Pat. No. 5,661,189 (to Unilever) discloses mixtures of anionic, cationic, amphoteric, nonionic, zwitterionic surfactants, along with benefit agents, thickening agents an small amounts of soap. These references are incorporated herein by reference for their general disclosure and compounding methods.

SUMMARY OF THE INVENTION

The present invention has found that hair treatment compositions containing micronized potato particles and clathrates may be effective in removing fresh chlorine from hair in a liquid composition. It is proposed that compositions that also contain at least 1% of the micronized potato particles, 1% by weight of clathrate, at least 0.01% by weight anionic surfactant and cationic surfactant present in a ratio of at least 15:1 to the anionic surfactant and/or amphoteric surfactant.

DETAILED DESCRIPTION OF THE INVENTION

The smell and effects of chlorine on human hair after using swimming pools, which almost always have chlorine present (e.g., usually as a hypochlorite) as a disinfectant/antibacterial agent, is more than annoying as it can be damaging to the skin and hair.

It is an old cooking tale that when a dish is over-salted, the addition of potato into the dish, especially soup, can remove the salt. It is proposed that potato particles, along with clathrates, another compound that is herein proposed to assist in retaining chlorine and hypochlorite in solution, might be effective in reducing the amount of chlorine retained in hair after swimming.

The proposed composition is 1% of the micronized potato particles and 1% by weight of clathrate in an aqueous carrier. A preferred composition would also comprise at least 0.01% by weight anionic surfactant and cationic surfactant present in a ratio of at least 15:1 to the anionic surfactant and/or amphoteric surfactant.

An excellent method of providing micronized particles of potato (dried and shredded, and milled to an initial small size) and/or clathrates (alone or mixed with the potato particles is described in U.S. Pat. No. 6,555,139 (Sharma), which is incorporated herein by reference. This process is particularly good in providing potato particles or potato/clathrate particles having sized of less than 50 microns, and preferably less than 10 microns. Particles of potato may also be made by milling, preferably by freeze-drying the potato, then milling the dried particles by any physical process of milling, such as ball milling. The potato may be chopped into smaller particles before freeze-drying and milling.

Clathrates are also called gas hydrates. Hydrates were discovered in 1810 by Sir Humphrey Davy, and were considered to be a laboratory curiosity. In the 1930s clathrate formation turned out to be a major problem, clogging pipelines during transportation of gas under cold conditions. Gas hydrates, also called clathrates, are crystalline solids which look like ice, and which occur when water molecules form a cage-like structure around smaller 'guest molecules'. The most common guest molecules are methane, ethane, propane, isobutane, normal butane, nitrogen, carbon dioxide and hydrogen sulfide, of which methane occurs most abundantly in natural hydrates. Water crystallizes in the cubic system in clathrates, rather than in the hexagonal structure of normal ice. Several different hydrate structures are known, with a preferred structure having the unit cell contains 46 molecules of water and up to eight molecules of methane [$(CH_4)\cdot 5.75(H_2O)$], but not all cages are occupied.

The methane in gas hydrates is dominantly generated by bacterial degradation of organic matter in low oxygen environments.

As the cationic surface active agent as the component in the hair-care toiletry composition of the present invention, any one among those used in conventional toiletry compositions can be used. There can be named, for example, alkyltrimethylammonium chlorides, stearyltrimethylammonium chloride, lauryltrimethylammonium chloride, cetyltrimethylammonium chloride, tallow alkyltrimethylammonium chloride, behenyltrimethylammonium chloride, stearyltrimethylammonium bromide, behenyltrimethylammonium bromide, distearyldimethylammonium chloride, dilauryldimethylammonium chloride, dioctyldimethylammonium chloride, polyoxyethylene oleylmethylammonium chloride, benzalkonium chloride, stearyl dimethyl benzylammonium chloride, lanolin-derived quaternary ammonium salts, stearic acid diethylaminoethylamide, stearic acid dimethylaminopropylamide, propyldimethylhydroxypropylammonium behenic acid amide and the like.

The compounding amount of the cationic component in the hair-care toiletry composition of the present invention is preferably 0.15-20% by weight or, more preferably, 0.25-10% by weight in order to impart the hair with good feel. When the compounding amount is smaller than 0.15% by weight and in a ratio of less than 15:1 for the anionic surfactant, the rate of chlorine leaching is too low. It is hypothesized, without relying on the effect for purposes of patentability, that the higher concentration of cationic surfactant attracts chlorine and especially hypochlorite into solution where it can be bound by the clathrate. Conditioning effects to the hair would be insufficient in an excess over 20% by weight.

As the anionic surface active agent and/or the amphoteric surface active agent as the component used in the present invention, any one of those used in conventional toiletry compositions can be used. There can be named, for example, as an anionic surface active agent, saturated or unsaturated fatty acid soaps, polyoxyethylene sulfate ester salts, .alpha.-acylsulfate ester salts, alkylsulfonate salts, alkylarylsulfonate salts, .alpha.-olefinsulfonate salts, alkylbenzenesulfonate salts, alkylnaphthalenesulfonate salts, alkanesulfonate salts, alkyl- or alkenylsulfate salts, alkylamide sulfate salts, alkyl- or alkenylphosphate salts, alkylamidephosphate salts, alkyloylalkyl taurine salts, N-acylaminoacid salts, sulfosuccinic acid salts, alkylether carboxylic acid salts, amidoether carboxylic acid salts, .alpha.-sulfofattyacid ester salts and the like.

As the amphoteric surface active agent, there can be named those of the carboxybetaine type, amidobetaine type, sulfobetaine type, hydroxysulfobetaine type, amidosulfobetaine type, phosphobetaine type, aminocarboxylic acid salt type, imidazoline derivative type, amidoamine type and the like. When both of the anionic surface active agent and the amphoteric surface active agent are used in combination as the component, meanwhile, the compounding proportion of both can be freely selected.

The compounding amount of the anionic/amphoteric component in the hair-care toiletry composition of the present invention is preferably 0.01-2% by weight or, more preferably, 0.005-1% by weight in order to impart the hair with good feel. When the compounding amount is smaller than 0.005% by weight, the conditioning effects to the hair would be insufficient while an excess over 2% by weight would result in adverse effects on the potato/clathrate antichlorine effects.

The polymeric compound for hair fixing as the component in the hair-care toiletry composition of the present invention includes those polymeric compounds of the amphoteric, anionic, cationic and non-ionic types and there can be named polyvinylpyrrolidones, vinylpyrrolidone/vinyl acetate copolymers, vinylpyrrolidone/vinyl acetate/vinyl propionate ternary copolymers, vinyl pyrrolidone/alkylamino(meth) acrylate (quaternary chloro) copolymers, vinyl pyrrolidone/alkyl (meth)acrylate/(meth)acrylic acid copolymers, vinyl pyrrolidone/alkylamino(meth)acrylate/vinyl caprolactam copolymers, vinyl pyrrolidone/methyl vinyl imidazolium chloride and the like as the vinyl pyrrolidone-based polymeric compound; methyl vinyl ether/maleic anhydride alkyl half ester copolymers and the like as the acidic vinyl ether-based polymeric compound; vinyl acetate/crotonic acid copolymers, vinyl acetate/crotonic acid/vinyl neodecanoate copolymers, and the like as the acidic polyvinyl acetate-based polymer; (meth)acrylic acid/alkyl (meth)acrylate copolymers, (meth)acrylic acid/alkyl (meth)acrylate/ alkyl acrylamide copolymers and the like as the acidic acrylic polymeric compound; N-methacryloylethyl-N,N-dimethylammonium.multidot..alpha.-N-met-hyl-carboxybetaine/alkyl (meth)acrylate copolymers, hydroxypropyl (meth)-acrylate/butyl aminoethyl methacrylate/acrylic acid octylamide copolymerds and the like as the amphoteric acrylic-based polymeric compound. In addition, natural polymeric compounds such as cellulose or derivatives thereof, keratin and collagen or derivatives thereof and the like can also be used satisfactorily.

A suitable definition for "detergent" as used herein is a synthetic water soluble cleansing preparation or compound that emulsifies oils and holds dirt in suspension. Early detergents were long chain alkyl groups with sulfonate or phosphonate end groups. Typical, but non-limiting examples of detergents useful in this invention include but are not limited to pareth-15-9, lauramide DEA, cocamide DEA, polysorbate-80, sodium laureth sulfate, sodium lauryl sulfate, ammonium lauryl sulfate, amphoteric-1, TEA-lauryl sulfate, TEA-laureth sulfate.

Examples of the counter ions of the anionic residues of these anionic surfactants include alkali metal ions such as a sodium ion, a potassium ion, etc.; alkaline earth metal ions such as a calcium ion, a magnesium ion, etc.; an ammonium ion; and alkanol amines containing 1 to 3 alkanol groups having 2 to 3 carbon atoms (such as monoethanolamine, diethanolamine, triethanolamine and triisopropanolamine).

Among the above anionic surfactants, those listed below are particularly preferred: (2) alkyl ether sulfates, (3) alkyl sulfates, (6) saturated or unsaturated fatty acid salts, (9) acylated amino acids, (10) surfactants of phosphoric monoester type, and (11) sulfosuccinic esters. Specific examples of particularly preferred ones are sodium polyoxyethylene laurylether sulfates (2 to 3 moles on average of ethylene oxide have been added), laurylsulfuric acid triethanolamines, sodium salts of coconut oil fatty acids, coconut oil aliphatic amide ether sulfates, lauroyl-N-methyltaurines, lauroyl-N-methyl-beta-alanines, disodium N-myristoyl-L-glutamates, lauroyl-beta-alanines, disodium polyoxyethylene laurylsulfosuccinates (3 to 7 E.O.), laurylphosphoric acids, N-lauroyl-N'-carboxymethyl-N'-(2-hydroxyethyl)eth-ylenediaminetriethanolamine salts, and N-lauroyl-N-(2-hydroxyethyl)-N',N'-bis(carboxymethyl)-ethylenediamine sodium salts.

These anionic surfactants are used singly or in combination of two or more. When they are used in a proportion from 1 to 20% by weight, preferably from 3 to 15% by weight, based on the total weight of the composition, excellent lathering ability and high conditioning effects are obtained.

Components of water-soluble polymers, which can be used in the present invention may be naturally occurred, semi-synthetic, or synthetic polymers. Moreover, any one of cationic polymers, anionic polymers, nonionic polymers can be used. Examples of naturally-occurred water-soluble polymers include vegetable polymers such as gum arabic, tragacanth gum, galactan, guar gum, carob gum, caraya gum, carrageenan, pectin, agar, quince seeds (*Cydonia oblonga*), and glycyrrhizic acid; microorganism-derived polymers such as xanthane gum, dextran, succinoglucan, and pullulan; and protein hydrolysate polymers such as keratin decomposition derivatives, etc.

Examples of semi-synthetic water-soluble polymers include starch polymers such as cationic starch, carboxymethyl starch, and methylhydroxypropyl starch; cellulose polymers such as cationic cellulose derivatives, methylcellulose, nitrocellulose, ethylcelluloce, methylhydroxypropylcellulose, hydroxyethylcellulose, sodium cellulose sulfate, hydroxypropylcellulose, carboxymethylcellulose-Na (CMC), crystalline cellulose, and cellulose powders; alginate polymers such as sodium alginate and propylene glycol alginate; and cationic guar gum derivatives.

Examples of synthetic water-soluble polymers include homopolymers of diallyl quaternary ammonium salts; copolymers of diallyl quaternary ammonium salt/acrylic amide; quaternarized polyvinylpyrrolidone derivatives; polyvinylpyrrolidones; copolymers of vinylpyrrolidone and vinyl acetate, alkylaminoacrylate, etc.; lower alkyl half esters of a copolymer of methylvinyl ether and maleic anhydride, copolymers of vinyl acetate and crotonic acid, etc.; copolymers of acrylic acid and/or methacrylic acid and an acrylic alkyl ester and/or a methacrylic alkyl ester; copolymers of acrylic acid, acrylic alkyl ester, and N-alkylacrylic amide; amphoteric copolymers of dialkylaminoethyl methacrylate, dialkylaminoethyl acrylate, diactone acrylic amide, etc. and acrylic acid, methacrylic acid, acrylic alkyl ester, methacrylic alkyl ester, etc.; tertiary copolymers of acrylic hydroxypropyl, methacrylic butylaminoethyl, and acrylic octylamide; and copolymers of alkyl acrylamide, acryl ate, alkylaminoalkyl acrylamide, and polyethylene glycol methacrylate.

Among the above water-soluble polymers, particularly preferred are those containing an amino group or an ammonium group as linked to a polymer chain, or containing dimethyldiallylammonium halide as a monomer unit. Specific examples include homopolymers of diallyl quaternary ammonium salts, cationic cellulose derivatives, cationic starches, cationic guar gum derivatives, copolymers of diallyl quaternary ammonium salt/acrylic amide, and quaternary polyvinyl pyrrolidone derivatives.

| (Proposed Formulation) | wt % |
|---|---|
| Potato particle (5 microns) | 3 |
| Clathrate (Tetraisopentylammonium Iodide) | 1.5 |
| Monolauric polyethylene (20) glycol | 5 |
| Polyoxyethylene (18) laurylether | 12 |
| Lauroyl diethanol amide | 3 |
| Compound of a quaternary ammonium salt | 4 |
| Sodium acylglutamate | 6 |
| High molecular weight dimethylpolysiloxane aqueous emulsion | 1.0 |
| Cationic polymer | 0.15 |
| Anionic polymer | 0.005 |
| Sodium benzoate | 0.3 |
| Colorant | suitable amount |
| Perfume | suitable amount |
| Citric acid | suitable amount |
| Water | balance |

What is claimed is:

1. A method of reducing the chlorine or hypochlorite retained by hair after the hair has been immersed in an aqueous environment having at least 0.5 parts per million chlorine comprising treating the hair with a composition comprising:

at least 1% by total weight of the composition of potato particles having an average diameter of less than 10 microns when dried;

at least 1% by total weight of the composition of clathrate;

at least 1% by weight of surfactant;

and water;

and allowing the composition to remain on the hair for at least 10 seconds, then rinsing off the composition with water.

2. The method of reducing the chlorine or hypochlorite retained by hair as claimed in claim 1 wherein the composition further comprises at least 0.5% by weight cationic surfactant.

3. The method of reducing the chlorine or hypochlorite retained by hair as claimed in claim 2 wherein an anionic surfactant is present in an amount of at least 0.001% by weight of the composition.

4. The method of reducing the chlorine or hypochlorite retained by hair as claimed in claim 3 wherein the weight ration of the cationic surfactant to the anionic surfactant is at least 15:1.

\* \* \* \* \*